(12) United States Patent
Golmohammadi Ghane et al.

(10) Patent No.: US 11,235,319 B2
(45) Date of Patent: Feb. 1, 2022

(54) COMPACT ANALYTICAL DEVICE FOR AN ANALYTE DETECTION

(71) Applicants: Hamed Golmohammadi Ghane, Tehran (IR); Zohre Hamzei, Rasht (IR)

(72) Inventors: Hamed Golmohammadi Ghane, Tehran (IR); Zohre Hamzei, Rasht (IR)

(*) Notice: Subject to any disclaimer, the term of this patent is extended or adjusted under 35 U.S.C. 154(b) by 13 days.

(21) Appl. No.: 16/929,770

(22) Filed: Jul. 15, 2020

(65) Prior Publication Data
US 2020/0346207 A1 Nov. 5, 2020

Related U.S. Application Data

(60) Provisional application No. 62/874,527, filed on Jul. 16, 2019.

(51) Int. Cl.
*G01N 1/00* (2006.01)
*B01L 3/00* (2006.01)
*G01N 1/28* (2006.01)
*G01N 1/40* (2006.01)

(52) U.S. Cl.
CPC .............. *B01L 3/502* (2013.01); *G01N 1/286* (2013.01); *G01N 1/4077* (2013.01); *B01L 2200/10* (2013.01); *B01L 2300/023* (2013.01); *B01L 2300/0663* (2013.01)

(58) Field of Classification Search
None
See application file for complete search history.

(56) References Cited

U.S. PATENT DOCUMENTS

2004/0058401 A1* 3/2004 Bossy .............. G01N 33/54326
435/7.23

\* cited by examiner

*Primary Examiner* — Jyoti Nagpaul
(74) *Attorney, Agent, or Firm* — Bajwa IP Law Firm; Haris Zaheer Bajwa

(57) ABSTRACT

A compact device compact analytical device to perform main steps of analytical procedures comprises a driving part configured to be attached to a stirrer part or a centrifuge part, wherein the stirrer part is configured to mix at least one sample and the centrifuge part is configured to separate a component. Furthermore, an analyzer part is configured to produce analytical data.

12 Claims, 7 Drawing Sheets

COMPACT ANALYTICAL DEVICE FOR AN ANALYTE DETECTION

CROSS REFERENCE TO RELATED APPLICATION

The present invention application claims priority from U.S. Provisional Patent Application Ser. No. 62/874,527, filed on Jul. 16, 2019, entitled "FULLY INTEGRATED LAB ON A SMARTPHONE", which is incorporated by reference herein in its entirety.

TECHNICAL FIELD

The present application is related to a compact analytical device integrated onto a portable computing device for (bio)-chemical and clinical analytical analysis. In detail, the device may detect albumin, phenylalanine, glucose, and hematocrit in a blood sample. Also, the device is configured to conduct bacteriological testing.

BACKGROUND

Despite all the advances in development of new methods for clinical and chemical analysis, one of the main limitations of most (bio)analytical methods is their reliance on expensive, bulky, and sophisticated devices that limit their applications for in situ sample analysis and point-of-use (POU) purposes. Therefore, one promising frontier for (bio) analytical chemistry is the ever-increasing development of novel analytical methods and tools that are able to meet the intended analytical requirements through efficient and easy-to-use approaches with no need for expensive, large and sophisticated instruments, and trained operators to run the tests/equipment and interpret the results.

Among these, simplification, automation, and miniaturization of analytical devices and methods, and more recently, the coupling of analytical devices with new emerging and ubiquitous technologies such as smartphones have witnessed significant growth.

The universal availability, affordability, ease-of-use, portability, and other useful and beneficial features of smartphones as miniature computers with fast operating systems, high-quality cameras, large memories, powerful and rechargeable batteries, several wireless connectivity and data transferring modes, touch-screen, USB and audio ports, and so on, make them promising and appealing platforms or tools in analytical chemistry and particularly in (bio)sensing and (bio)diagnostics technology.

Although significant developments have already been reached in terms of smartphone applications in (bio)analytical chemistry, a substantial gap still remains in moving a compact analytical devices integrated onto a smartphone from purely sensing and data analyzing platforms toward more functional and integrated analytical devices that may fulfill most of the (bio)analytical/diagnostic procedures, which often require multiple-steps of mixing, separating, analyzing, and microscopy. Because of this obstacle, the applications of smartphone-based analytical devices are greatly limited, especially in resource-limited settings and at the point-of-care (POC) and POU, where access to routine laboratory equipment is usually either lacking or very limited. To overcome this access limitation, the development of new compact analytical devices integrated onto smartphone for performing main steps of (bio)analytical procedures is required, which are portable, easy-to-use, efficient, rapid and moreover needed small volumes of sample and reagents.

SUMMARY

This summary is intended to provide an overview of the subject matter of this patent, and is not intended to identify essential elements or key elements of the subject matter, nor is it intended to be used to determine the scope of the claimed implementations. The proper scope of this patent may be ascertained from the claims set forth below in view of the detailed description below and the drawings.

In one general aspect, the present disclosure is directed to an exemplary compact analytical device for performing main steps of analytical procedures. The exemplary compact analytical device may comprise a driving part comprising a chamber with at least two holes for holding at least two pillars, an armature, a motor speed controller, and a connection port, the driver part configured to be attached to a stirrer part or a centrifuge part, wherein: the stirrer part may be configured to mix at least one sample, the stirrer part including a stirrer plate, at least two pillars, a stirrer blade, and at least two magnets placed on two sides of the stirrer blade, and the centrifuge part may be configured to separate a component, the centrifuge part including a conical plate with at least two micro tube positions and two capillary tub positions. Furthermore, the exemplary compact analytical device may further comprise an analyzer part configured to produce analytical data, the analyzer part including a dark chamber with an image capturing aperture, at least one hole for an optical source, a connection port, and a strip hole configured to insert a strip holder. Also, the exemplary compact analytical device may further comprise a microscope part including a magnifying lens, a microscopy slid holder, at least two gears, and a light source, wherein the light source may be placed on an opposite side of the image capturing aperture within the dark chamber. Moreover, the exemplary compact analytical device may further comprise a portable computing device configured to quantify analytical data, the portable computing device including one or more processors, a memory, an image capturing device, and a charger port, and a frame configured to hold the analyzer part and the microscope part, the frame comprising a chamber with a connection port and a cover plate, wherein a first substrate of the cover plate may be configured to hold the portable computing device.

The above general aspect may have one or more of the following features. In an exemplary implementation, the pillars may be fixed on the holes of the chamber of the driving part. In an exemplary implementation, the pillars may be movable inside the holes of the chamber of the driving part. In an exemplary implementation, the pillars may comprise a first section and at least one second section configured to change a height level of the stirrer plate, wherein the second section of the pillars may be configured to move between a retracted position inside of the first section and an extended position outside of the first section. In an exemplary implementation, the stirrer plate may include a plurality of holes for holding more than one sample. In an exemplary implementation, the stirrer plate may be configured to hold one sample. In an exemplary implementation, a cone angle of the conical plate may be in a range of 30 to 60 degrees. In an exemplary implementation, the portable computing device may be configured to charge the compact analytical device. In an exemplary implementation, the device may be configured to analyze a body fluid. In an exemplary implementation, the device may be configured to conduct an analytical diagnosis of Phenylketonuria disease, point-of-care testing of glucose, hematocrit, and albumin, perform a bacteriological test, and diagnosis of Tuberculosis. In an exemplary implementation, the device may be configured to determine phenylalanine, glucose, albumin, or hematocrit level based on an analysis of a blood sample. In an exemplary implementation, the device may be configured to detect *Mycobacterium tuberculosis* bacteria in a sputum sample. In an exemplary implementation, the device may further comprise a phenylalanine assay kit comprising a bacterial cellulose substrate, a plurality of circle patterns embedded with quantum dot and Fe (III), wherein the plurality of circle patterns may print on a first surface of the bacterial cellulose substrate.

BRIEF DESCRIPTION OF THE DRAWINGS

The drawing figures depict one or more implementations in accordance with the present teachings, by way of example only, not by way of limitation. In the figures, like reference numerals refer to the same or similar elements.

DETAILED DESCRIPTION

Figure 1:
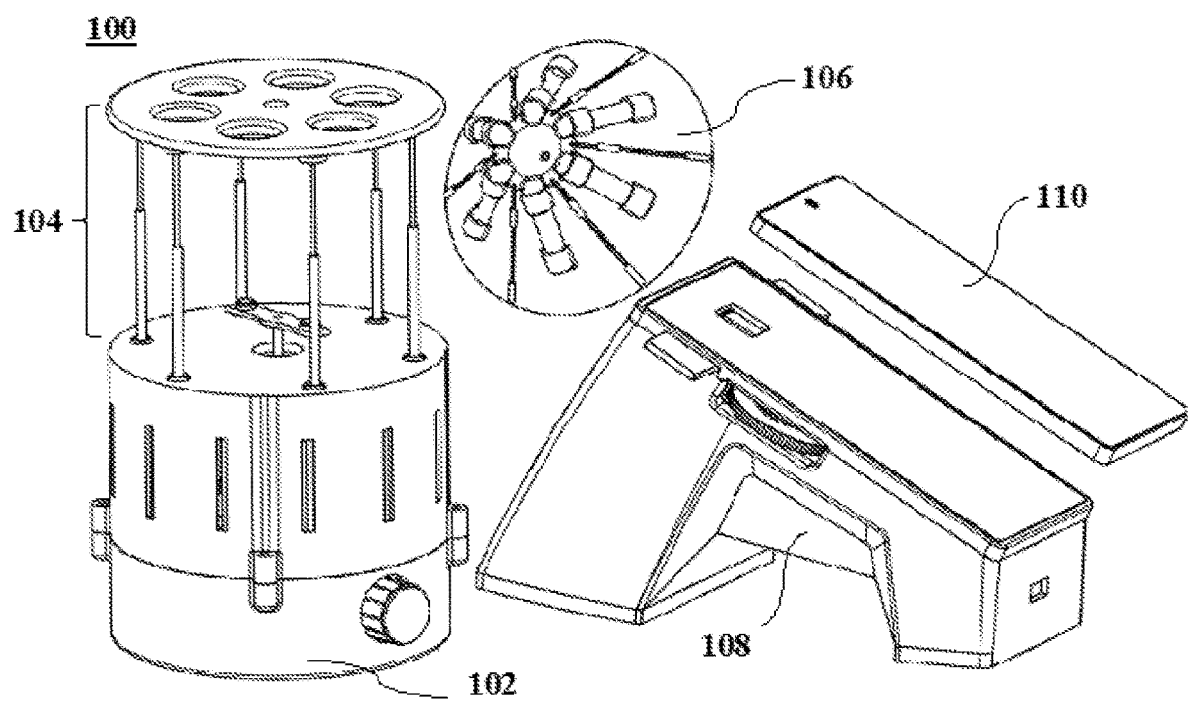
FIG. 1 illustrates an isometric view of a compact analytical device for performing an analytical procedure, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is, therefore, not to be taken in a limiting sense, and the scope of the present disclosure is defined only by the appended claims.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

In an exemplary embodiment, a compact analytical device for performing main steps of an analytical procedure may comprise a stirrer part configured to mix at least one sample, a centrifuge part configured to separate a component, and a driving part such that the driving part may be configured to be attached to the stirrer part or the centrifuge part to provide a motive power. In an exemplary embodiment, the device further may comprise a microscope part and/or an analyzer part for detecting and/or analyzing a sample. In an exemplary embodiment, the device also may comprise a frame, wherein the frame may be configured to hold the analyzer and the microscope part.

In an exemplary embodiment, an exemplary compact analytical device may further integrate onto a portable computing device. In an exemplary embodiment, the portable computing device may comprise a battery, one or more processors, at least one memory, an image capturing device, a charger port, a wireless connectivity, and a data transferring platform. The portable computing device may be configured to quantify the analytical data as well as capture an image. In one or more exemplary embodiments, the portable computing device may further comprise a software app to quantify analytical data and produce a value. In an exemplary embodiment, the portable computing device may also transfer the value utilizing a data transferring platform of the computing device to a subject. The subject may refer to a physician, a clinical expert, a clinical laboratory expert, a patient, etc.

In another exemplary embodiment, an exemplary portable computing device may be further configured to charge the device and provide (an) electrical power for the device such that the portable computing device may be connected to the driving part, or the analyzer part, or the microscope part through the charger port. In an exemplary embodiment, the portable computing device may be a smartphone or a tablet.

In an exemplary embodiment, an exemplary frame of the device may comprise a chamber with a connection port and a cover plate with a hole. In an exemplary embodiment, a top of the cover plate may be configured to hold the portable computing device. In an exemplary embodiment, the image capturing device of the portable computing device may match in shape a hole of the cover plate. In an exemplary embodiment, the chamber and the cover plate of the frame may be also fabricated by utilizing one of a 3D-printing process, an injection molding process, a laser cutting process, and other processes that are known for those skilled in the art.

In an exemplary embodiment, an exemplary driving part of the compact analytical device may comprise a chamber with at least two holes for holding at least two pillars, an armature, a motor speed controller, and a connection port. In one or more exemplary embodiments, the connection port may be configured to provide the electrical power for the motor speed controller. In an exemplary embodiment, the motor speed controller of the driving part may be connected to the charger port of the portable computing device through the connection port. In an exemplary embodiment, the connection port may be, for example, a USB port.

In an exemplary embodiment, the chamber with at least two holes for holding at least two pillars may be fabricated by utilizing one of a 3D-printing process, an injection molding process, a laser cutting process, and other processes that are known for those skilled in the art.

In an exemplary embodiment, an exemplary stirrer part may comprise a stirrer plate, at least two pillars, a stirrer blade, and at least two magnets placed on two sides of the stirrer blade. In an exemplary embodiment, the stirrer plate may comprise a plurality of container holding holes which may each hold a respective container which may include a sample. In an exemplary embodiment, the container may comprise, for example, not limited, a tube, a micro tube, a vial, a micro vial, a penicillin bottle, a falcon, etc. In another exemplary embodiment, the stirrer plate may be configured to hold one container containing a sample and the container may be a laboratory flask, for example, but not limited to, a conical flask, a Florence flask, a volumetric flask, or a laboratory container such as a beaker. In an exemplary embodiment, the pillars may be configured to adjust or change a height level of the stirrer plate. In an exemplary embodiment, the height level of the stirrer plate may refer to a distance from a bottom surface of the stirrer plate to a top surface of the magnets. In an exemplary embodiment, each pillar may also comprise a first section and at least one second section where the second section may be mounted in the first section. In an exemplary embodiment, the first section of each pillar may be attached to the chamber of the driving part through the hole. In an exemplary embodiment, the first section may be fixed on the chamber of the driving part. In another exemplary embodiment, the first section of each pillar may be movable inside the hole of the chamber of the driving part. In an exemplary embodiment, the second section of each pillar may be configured to move between a retracted position inside of the first section and an extended position outside of the first section. In one or more exemplary embodiments, the pillars may be, for example, but not limited to, adjustable rods, telescopic rods, telescopic stands, adjustable stands, adjustable bar, etc. In an exemplary embodiment, the stirrer blade with at least two magnets may be attached to an armature of a driving part to rotate the stirrer blade and the magnets. In an exemplary embodiment, a magnet may be configured to mix the sample. In an exemplary embodiment, the magnet may be put inside the container and may mix the sample due to rotational motion of the stirrer blade with two magnets and resulting rotational magnetic field.

In an exemplary embodiment, an exemplary centrifuge part of the compact analytical device may comprise a conical plate with at least two micro tube positions and two capillary tub positions. In an exemplary embodiment, the micro-tube positions and capillary tube positions may be placed on an outer surface of the conical plate at a same distance that may balance the conical plate. In an exemplary embodiment, the conical plate may further comprise a central bore. In an exemplary embodiment, the central bore may be configured to attach to the armature of the driving part. In an exemplary embodiment, the armature may be configured to provide a centrifugal force to separate the component.

In an exemplary embodiment, the conical plate of the centrifuge part may further have a cone angle. In an exemplary embodiment, the cone angle of the conical plate may be in a range of 30 to 60 degrees. In another exemplary embodiment, a cone angle of the conical plate may be in a range of 40 to 55 degrees. In an exemplary embodiment, a cone angle of the conical plate may refer to an angle between the central bore of the conical plate and the micro tube position or capillary tube position.

In an exemplary embodiment, a conical plate of an exemplary centrifuge part with at least two micro tube positions and at least two capillary tub positions may be fabricated by utilizing one of a 3D-printing process, an injection molding process, a laser cutting process, and other processes that are known for those skilled in the art.

In an exemplary embodiments, an exemplary analyzer part may comprise a dark chamber with an image capturing aperture, at least one hole for an optical source, a connection port, a strip hole, and a strip holder. In an exemplary embodiment, the image capturing aperture may be configured to be matched to the image capturing device and the hole of the cover plate such that the aperture may allow the image capturing device to capture an image from a sample. In an exemplary embodiment, the strip hole may be configured to insert the strip holder under the optical source such that the ambient light may not enter the dark chamber from the strip hole. In an exemplary embodiment, the optical source may be configured to provide an irritation light. In an exemplary embodiment, the strip holder may be configured to hold a sample. In an exemplary embodiment, the sample may contain a reagent such that the reagent may irritate by the irritation light and produce a color as analytical data. In an exemplary embodiment, the analyzer part may be configured to produce analytical data by utilizing irritation light on the sample containing the reagent within the strip holder. In an exemplary embodiment, analytical data may be a colorimetric data or a fluorometric data. In an exemplary embodiment, the optical source may comprise a lamp, a UV lamp, a LED lamp, etc. In one or more exemplary embodiments, the LED lamp may include a white LED and/or an Ultra-Violet (UV) LED. In an exemplary embodiment, the optical source for producing the colorimetric data may be a white LED. In another exemplary embodiment, a UV LED may be configured to provide a UV irritation light such that the UV irritation light may irritate a fluorescent reagent to produce the fluorometric data.

In an exemplary embodiment, the dark chamber and the strip holder may be fabricated by utilizing one of a 3D-printing process, an injection molding process, a laser cutting process, and other processes that are known for those skilled in the art.

In an exemplary embodiment, an exemplary microscope part may comprise a magnifying lens, a microscopy slid holder, at least two gears, a light source, and a light diffuser. In an exemplary embodiment, the light source may be placed on an opposite side of the image capturing aperture within the dark chamber. In an exemplary embodiment, the magnifying lens may be a stick-on magnifying lens and the magnifying lens may be attached onto an exterior surface of the image capturing device of the portable computing device. In an exemplary embodiment, a sample may be placed on a top surface of the slide holder. In an exemplary embodiment, the slide holder may be put under the hole of cover plate of the frame as well as in front of the magnifying lens and the image capturing device to detect a morphological characterization of the sample and capture an image from the sample. In an exemplary embodiment, the morphological characterization of the sample may include a size, a shape, a color, or a brightness. In an exemplary embodiment, two gears may be connected to the frame. In an exemplary embodiment, the gears may be configured to laterally move the slide holder under the hole of cover plate such that the sample on the top surface of the slide holder may be placed in front of the magnifying lens attached to image capturing device of the portable computing device. In an exemplary embodiment, the light diffuser for uniform illumination distribution may comprise different types of diffuser sheets, for example, an acrylic sheet, a polycarbonate sheet, a poly (ethylene terephthalate glycol) (PETG) sheet, etc.

In an exemplary embodiment, the compact analytical device consistent with one or more exemplary embodiments of the present disclosure may be configured to colorimetric/fluorometric analyze chemical, (bio)chemical and bacteriological parameters in a biological fluid sample, a water sample, a soil sample, a plant sample, and/or a food sample. In an exemplary embodiment, the biological fluid sample may be a blood sample, a urine sample, a sweat sample, and/or a saliva sample.

In an exemplary embodiment, an exemplary compact analytical device may be configured to determine a phenylalanine, glucose, albumin, and/or hematocrit level in the blood sample. In an exemplary embodiment, the determination of the phenylalanine, glucose, and hematocrit may be utilized for diagnosing Phenylketonuria (PKU), Diabetes, and Anemia, respectively.

In an exemplary embodiment, an exemplary compact analytical device may be configured to do an early diagnosis of tuberculosis (TB) disease through detection of *Mycobacterium tuberculosis* bacteria.

In an exemplary embodiment, an exemplary compact analytical device may further comprise an assay kit to diagnose a phenylaniline level in blood samples. In an exemplary embodiment, the assay kit may comprise a cellulose substrate, preferably a bacterial cellulose substrate, and a plurality of circle patterns embedded with quantum dots and Fe (III). In an exemplary embodiment, the circle patterns may be printed on a top of the cellulose substrate. In an exemplary embodiment, the circle patterns may have a diameter in a range of 1 mm to 5 mm.

In an exemplary embodiment, FIG. 1 illustrates an isometric exemplary view of a compact analytical device 100, consistent with one or more exemplary embodiments of the present disclosure. As illustrated in FIG. 1, the compact analytical device 100 may comprise a driving part 102. In an exemplary embodiment, the driving part 102 may be configured to be attached to a stirrer part 104. In an exemplary embodiment, the driving part 102 may be configured to be attached to a centrifuge part 106. Furthermore, the device 100 may comprise a frame 108 which may be configured to hold an analyzer part (not illustrated) and a microscope part (not illustrated). In an exemplary embodiment, a portable computing device 110 may be integrated with the frame 108. In an exemplary embodiment, the portable computing device 110 may be configured to quantify analytical data. Moreover, the portable computing device 110 may be configured to charge the device 100.

Figure 2:
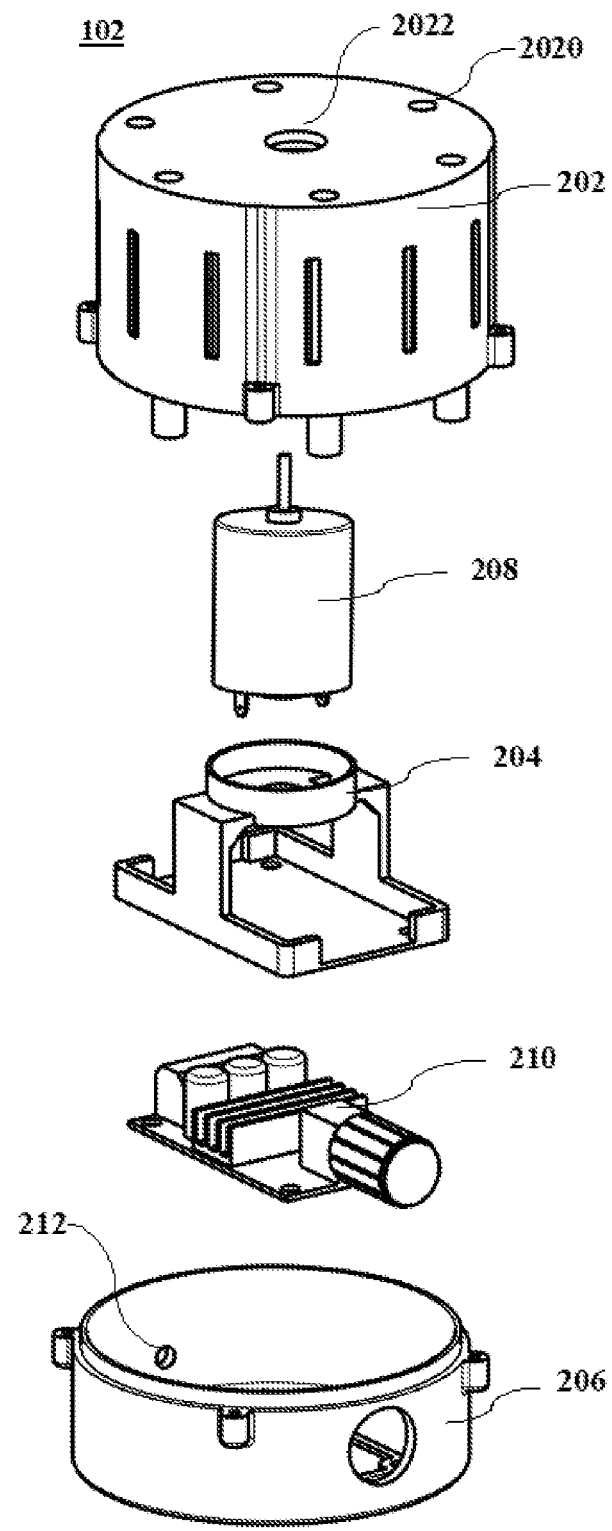
FIG. 2 illustrates an isometric view of a driving part of the compact analytical device for providing a motive power, consistent with one or more exemplary embodiments of the present disclosure.

In an exemplary embodiment, FIG. 2 illustrates an isometric exemplary view of driving part 102, consistent with one or more exemplary embodiments of the present disclosure. As illustrated in FIG. 2, the driving part 102 may comprise a first chamber 206 which may house or store a motor speed controller 210 and a connection port 212, a second chamber 204 for holding an armature 208, and a third chamber 202 that may be configured to be detachable to the first chamber 206. In an exemplary embodiment, second chamber 204 may be put into the third chamber 202. In an exemplary embodiment, third chamber 202 may include six holes 2020 for holding six pillars of a stirrer part 104. In an exemplary embodiment, the six holes 2020 may be peripherally placed on a top surface of the third chamber 202. In one or more exemplary embodiments, the third chamber 202 may comprise a hole 2022 for the armature at a center of the top surface of third chamber 202. In an exemplary embodiment, the armature through the hole 2024 may be attached to the stirrer part (not illustrated) or the centrifuge part (not illustrated).

In an exemplary embodiment the first chamber 206, the second chamber 204, and the third chamber 202 of the driving part 102 may be fabricated by utilizing one of a 3D-printing process, an injection molding process, a laser cutting process, and other processes that are known for those skilled in the art.

Figure 3:
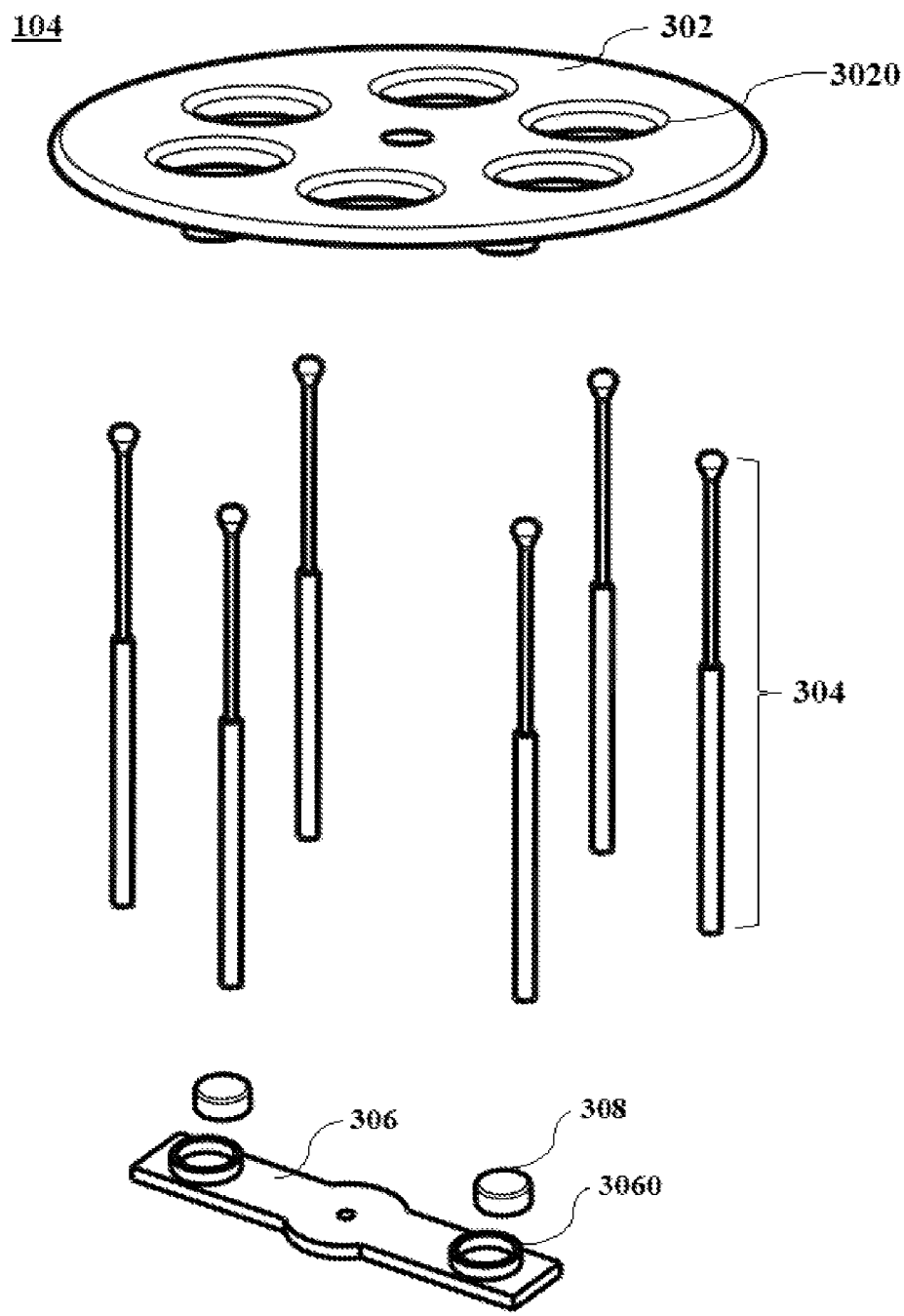
FIG. 3 illustrates an isometric view of a stirrer part of the compact analytical device for mixing a sample, consistent with one or more exemplary embodiments of the present disclosure.

In an exemplary embodiment, FIG. 3 illustrates an isometric exemplary view of the stirrer part 104, consistent with one or more exemplary embodiments of the present disclosure. As illustrated in FIG. 3, the stirrer part 104 may comprise a stirrer plate 302 with six holes 3020 for holding six containers (not illustrated), six pillars 304, a stirrer blade 306, and two magnets 308 placed on two end sides 3060 of the stirrer blade 306. In an exemplary embodiment, the stirrer blade 306 may be connected to the armature 208 of the driving part 102 and stirrer plate 302 may be connected to the top surface of the third chamber 202 of the driving part 102 utilizing six pillars 304.

Figure 4A:
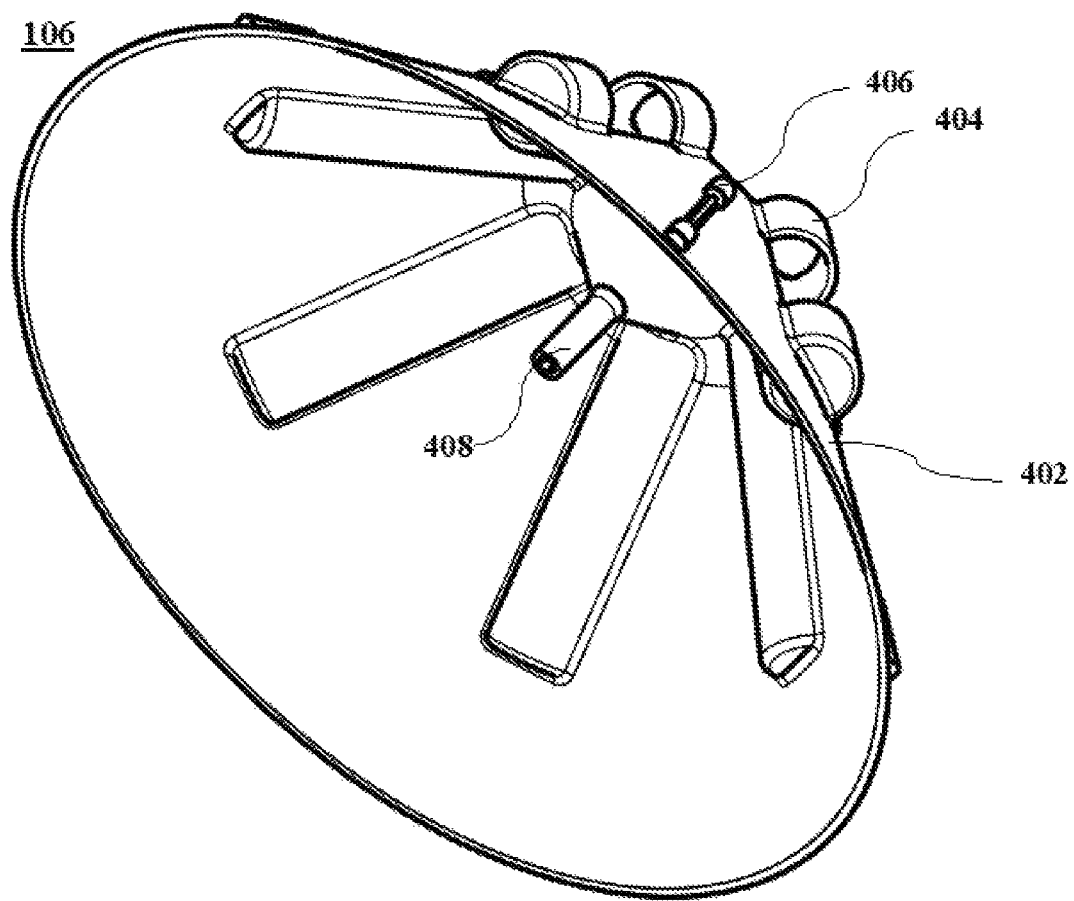
FIG. 4A illustrates a bottom view of a conical plate of a centrifuge part of the compact analytical device for separating a component, consistent with one or more exemplary embodiments of the present disclosure.
Figure 4B:
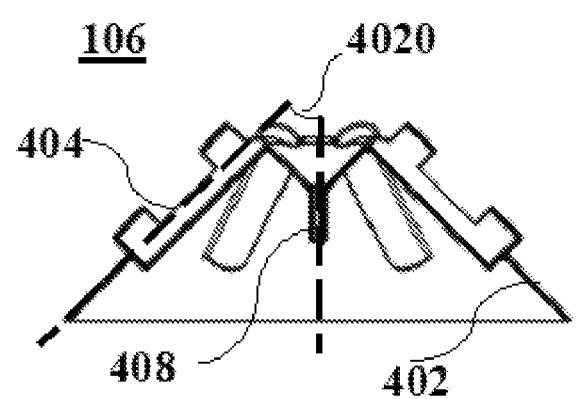
FIG. 4B illustrates a cross-section view of a conical plate of a centrifuge part of the compact analytical device for separating a component, consistent with one or more exemplary embodiments of the present disclosure.

In an exemplary embodiment, FIG. 4A illustrates a bottom exemplary view of a conical plate 402 of the centrifuge part 106, consistent with one or more exemplary embodiments of the present disclosure. As illustrated in FIG. 4A, the conical plate 402 of the centrifuge part 106 may comprise six micro-tube positions 404 and six capillary tube positions 406 with equal distance between each micro-tube position 404 and each capillary tube position 406, and a central bore 408. In an exemplary embodiment, the conical plate 402 may be attached to the armature 208 of the driving part 200 via the central bore 408. Furthermore, in an exemplary embodiment, FIG. 4B illustrates a cross-sectional exemplary view of the conical plate 402 of the centrifuge part 106, consistent with one or more exemplary embodiments of the present disclosure. As illustrated in FIG. 4B, the conical plate 402 of the centrifuge part 106 may comprise a cone angle 4020. In an exemplary embodiment, the cone angle 4020 of the conical plate 402 may refer to an angle between the central bore 408 and the micro-tube position 404 or the capillary position 406. In one or more exemplary embodiments, the cone angle 4020 may be 45 degrees.

Figure 5A:
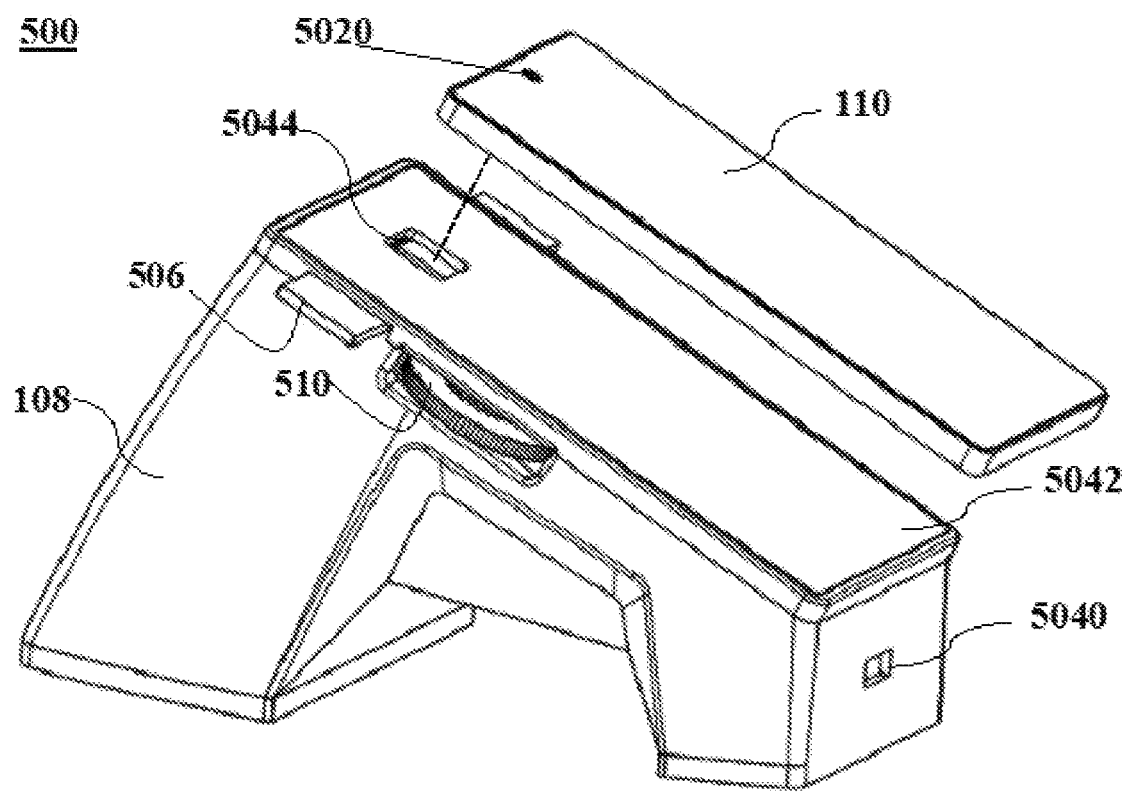
FIG. 5A illustrates an isometric view of a phone-integrated apparatus of the compact analytical device for analyzing and detecting an analyte in a sample, consistent with one or more exemplary embodiments of the present disclosure.
Figure 5B:
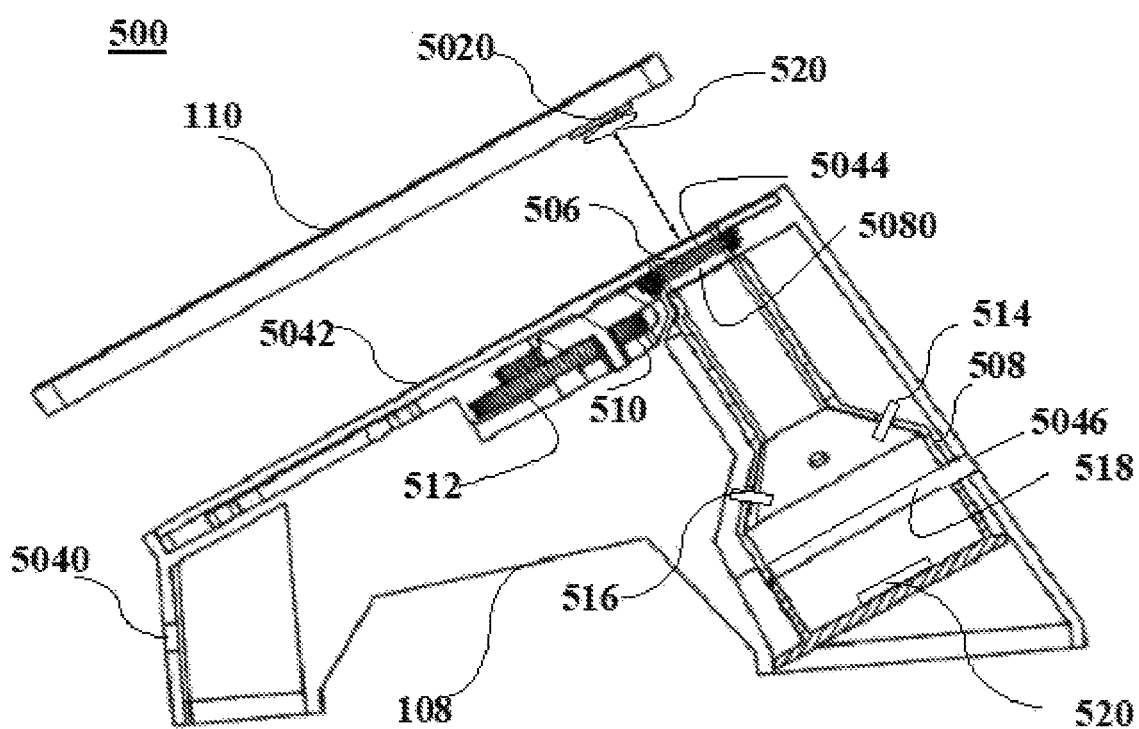
FIG. 5B illustrates a cross-section view of a phone-integrated apparatus of the compact analytical device for analyzing and detecting an analyte in a sample, consistent with one or more exemplary embodiments of the present disclosure.

FIG. 5A illustrates an isometric exemplary view of a phone-integrated apparatus 500 for analyzing and/or detecting a sample, consistent with one or more exemplary embodiments of the present disclosure. FIG. 5B illustrates a cross-section view of a phone integrated apparatus 500 for analyzing and/or detecting a sample, consistent with one or more exemplary embodiments of the present disclosure.

In an exemplary embodiment, the phone-integrated apparatus 500 may comprise a frame 108 with a connection port 5040 and a cover plate 5042. In an exemplary embodiment, the cover plate 5042 may include an aperture 5044. the phone 102 may be placed on a top surface of the cover plate 5042 wherein the camera 5020 of the phone 110 may be matched to the aperture 5044.

In an exemplary embodiment, the frame 108 of the phone-integrated apparatus 500 may further include a dark chamber 508, a strip holder 518 for holding a sample that may be removably disposed within the dark chamber 508 with an image capturing aperture 5080, a UV LED 514 that may be disposed within the dark chamber 508, a white LED 516, 520 that may be disposed within the dark chamber 508, two gears 510, 512 such that the gears may be connected to the frame 108, a slide holder 506 that may be disposed under the aperture 5044 of the cover plate 5042. In an exemplary embodiment, the frame 108 may further include a hole 5046 such that the hole may apply for insertion of the strip holder 518. In another exemplary embodiment, the phone-integrated apparatus 500 may further include a magnifying lens 520 such that the lens 520 may be attached to the camera 5020 of the phone 110.

EXAMPLES

Example 1: Post-of-Care Testing of Hematocrit, Glucose, and Albumin

In Example 1, a post-of-care testing of hematocrit, glucose, and albumin was carried out consistent with the teachings of the exemplary embodiment of the present disclosure. In this case, a blood sample was taken from a person. For measurement of a hematocrit level, a drop blood sample was first pulled into a capillary tube, preferably, a heparinized capillary. Following that, in order to separate plasma from the blood sample, the capillary tube was placed in an exemplary capillary position of an exemplary centrifuge part of an exemplary compact analytical device and centrifuge separation was carried out for 4 min at 2500 rpm. Then, the level of hematocrit was measured by using a micro-hematocrit reader as the ratio of the volume of compact analytical packed red blood cells to a total volume of the blood sample.

For measurement of a glucose level in the blood sample, 1 μl of the plasm that was separated from the blood sample was mixed with 100 μl of a pre-mixed standard reagent using an exemplary stirrer part of an exemplary device to prepare a mixture. Then, the mixture was transferred into an exemplary strip holder. The strip holder was then left 20 min to allow the glucose react with the standard pre-mixed reagent. After that, the strip holder was placed within a strip hole of an exemplary analyzer part in front of an exemplary image capturing device and under a white LED. Following that, a plurality of images of the mixture were captured under the white LED irradiation and stored in a memory of an exemplary phone. Then, the images were color analyzed (preferably in RGB mode) utilizing an exemplary software application embedded on memory of an exemplary phone to determine the glucose level of the sample.

Furthermore, for measurement of an albumin level in a blood sample, in order to separate the plasma, the blood sample was transferred into heparinize capillary tube and then was placed in an exemplary capillary position of an exemplary conical plate of an exemplary centrifuge part. Following that, 1 μl of the separated plasma from the blood sample was put into an exemplary container and was mixed with 100 μl of a standard pre-mixed albumin reagent using an exemplary stirrer part of an exemplary compact analytical device to prepare a mixture. Then, the mixture was transferred into an exemplary strip holder. After that, the strip holder was left for 10 minutes to allow the albumin react with the standard albumin reagent. Afterward, the strip holder was placed within an exemplary strip hole of an exemplary analyzer part. The strip holder containing the mixture was put in front of an exemplary image capturing device and under a white LED. Following that, a plurality of images of the mixture were captured under the white LED irradiation and stored in a memory of an exemplary phone. Then, the images were color analyzed (preferably in RGB mode) utilizing an exemplary software application embedded on memory of an exemplary phone to determine the albumin level of the sample.

Example 2: Determination of L-Phenylalanine

In Example 2, a procedure for determining of a phenylalanine was carried out consistent with the teachings of exemplary embodiments of the present disclosure. In this case, a drop blood sample which was taken by a blood sampling device (for example a lancet) and put into a heparinized capillary tube. The capillary tube was then placed in an exemplary capillary tube position in an exemplary conical plate of an exemplary centrifuge part for 3 min at 2500 rpm to produce a separated plasma. Following that, the separated plasma was isolated and transferred to an exemplary container. Then, 300 μl of the separated plasma was mixed with 5 mg of a magnetic molecular imprinted polymer (MMIP) in an exemplary stirrer part of an exemplary compact analytical device. After 2 min stirring at room temperature, the MMIP was separated by utilizing an exemplary centrifuge part of an exemplary compact analytical device at 2500 rpm for 2 min to prepared a separated MMIP containing phenylalanine. Then, the separated MMIP was mixed with 200 μl of isopropanol utilizing the exemplary stirrer part to prepare a mixture of isopropanol and a released phenylalanine. Afterward, isopropanol was centrifuged for 2 min at 2500 rpm using the exemplary centrifuge part to prepared a separated-released phenylalanine. After that, the separated-released phenylalanine was washed and diluted using purified water. Then, diluted phenylalanine was pipetted into an exemplary circle patterns of an exemplary assay kit and allowed to dry at ambient condition for 15 min. Afterward, the exemplary kit assay was placed within an exemplary analyzer part of an exemplary compact analytical device utilizing an exemplary strip holder such that the exemplary assay kit was placed under an exemplary UV LED lamp of the exemplary analyzer and in front of an exemplary image capturing device of an exemplary phone. Following that, a plurality of images of the exemplary circle patterns as test zones were captured under the UV LED irradiation and stored in a memory of an exemplary phone. Then, the images were color analyzed (preferably in RGB mode) utilizing an exemplary software application embedded on memory of an exemplary phone to determine the phenylalanine level.

Assay Kit Fabrication

An exemplary assay kit was fabricated for detection of phenylalanine in the blood samples. For fabrication of the assay kit, at first a wet bacterial cellulose (BC) nano papers were dewatered through sandwiching the nano papers between two filter papers and then was place in an oven with a temperature of 100 degrees for 2 hours to prepare a dried BC nano paper. Afterward, the dried BC paper was separated from one of the filter papers. Following that, a laser printer was configured to create a plurality of circular patterns. The patterns were printed via a printer toner on the dried BC nano paper film to prepare a BC substrate with plurality of the circular patterns. After separation of the BC substrate from the other filter paper, 5 μl of pre-mixed solution of the quantum dots, Fe (III), and Tris buffer which was prepared by utilizing an exemplary stirrer part of an exemplary compact analytical device, were drop-dried at ambient conditions into circular patterns as test zones to fabricate the assay kit.

Example 3: Bacteriological Test for Tuberculosis Diagnosis

In Example 3, a bacteriological test for tuberculosis diagnosis was carried out on a sputum sample consistent with the teachings of the exemplary embodiment of the present disclosure. In the case, the sputum sample was first concentrated through mixing with 4% NaOH using an exemplary stirrer part of an exemplary compact analytical device for 15 min and then centrifuging for 15 min at 2500 rpm using an exemplary centrifuge part of an exemplary compact analytical device. The concentrated sputum sample then neutralized with HCl. Following that, the neutralized sputum sample was stained by standard Ziesh-Neelsen and a slide of the sample was prepared for microscopic analyzing utilizing an exemplary microscope part of an exemplary compact analytical device. The slide was then placed in an exemplary slide holder of the exemplary microscope part and put under an exemplary magnifying lens attached to an exemplary image capturing device of an exemplary phone to capture an image for diagnosis of TB in the sputum sample.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood that the terms and expressions used herein have the ordinary meaning as is accorded to such terms and expressions with respect to their corresponding respective areas of inquiry and study except where specific meanings have otherwise been set forth herein. Relational terms such as first, second, and third and the like may be used solely to distinguish one entity or action from another without necessarily requiring or implying any actual such relationship or order between such entities or actions. The terms "comprises," "comprising," "include," "including," or any other variation thereof, are intended to cover a non-exclusive inclusion, such that a process, method, article, apparatus, or device that comprises a list of elements does not include only those elements but may include other elements not expressly listed or inherent to such process, method, article, apparatus, or device. An element proceeded by "a" or "an" does not, without further constraints, preclude the existence of additional identical elements in the process, method, article, or device that comprises the element. Moreover, "may" and other permissive terms are used herein for describing optional features of various embodiments. These terms likewise describe selectable or configurable features generally, unless the context dictates otherwise.

What is claimed is:

1. A compact analytical device, comprising:
   a driving part comprising a chamber with at least two holes for holding at least two pillars, an armature, a motor speed controller, and a connection port, the driver part configured to be attached to a stirrer part or a centrifuge part, wherein:
     the stirrer part configured to mix at least one sample, the stirrer part including a stirrer plate, at least two pillars, a stirrer blade, and at least two magnets placed on two sides of the stirrer blade; and
     the centrifuge part configured to separate a component, the centrifuge part including a conical plate with at least two micro tube positions and at least two capillary tub positions;
   an analyzer part configured to produce analytical data, the analyzer part including a dark chamber with an image capturing aperture, at least one hole for an optical source, a connection port, and a strip hole configured to insert a strip holder;
   a microscope part including a magnifying lens, a microscopy slid holder, at least two gears, and a light source, wherein the light source is placed on an opposite side of the image capturing aperture within the dark chamber;
   a portable computing device configured to quantify analytical data, the portable computing device including one or more processors, a memory, an image capturing device, and a charger port; and
   a frame configured to hold the analyzer part and the microscope part, the frame comprising a chamber with a connection port and a cover plate, wherein a first substrate of the cover plate is configured to hold the portable computing device.

2. The device according to claim 1, wherein the pillars are movable inside the holes of the chamber of the driving part.

3. The device according to claim 1, wherein the pillars comprise a first section and at least one second section configured to change a height level of the stirrer plate, wherein the second section of the pillars configured to move between a retracted position inside of the first section and an extended position outside of the first section.

4. The device according to claim 1, wherein the stirrer plate includes a plurality of holes for holding more than one sample.

5. The device according to claim 1, wherein the stirrer plate is configured to hold one sample.

6. The device according to claim 1, wherein a cone angle of the conical plate is in a range of 30 to 60 degrees.

7. The device according to claim 1, wherein the portable computing device is configured to charge the compact analytical device.

8. The device according to claim 1, wherein the device is configured to analyze a body fluid.

9. The device according to claim 1, wherein the device is configured to conduct an analytical diagnosis of Phenylketonuria disease, point-of-care testing of glucose, hematocrit, and albumin, perform a bacteriological test, and diagnosis of Tuberculosis.

10. The device according to claim 1, wherein the device is configured to determine phenylalanine, glucose, albumin, or hematocrit level based on an analysis of a blood sample.

11. The device according to claim 1, wherein the device is configured to detect *Mycobacterium tuberculosis* bacteria in a sputum sample.

12. The device according to claim 1, further comprising a phenylalanine assay kit comprising a bacterial cellulose substrate, a plurality of circle patterns embedded with quantum dot and Fe (III), wherein the plurality of circle patterns is printed on a first surface of the bacterial cellulose substrate.

* * * * *